(12) United States Patent
Rüegg

(10) Patent No.: US 6,489,267 B1
(45) Date of Patent: Dec. 3, 2002

(54) HERBICIDAL COMPOSITION

(75) Inventor: Willy T. Rüegg, Gipf-Oberfrick (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/663,224

(22) Filed: Sep. 15, 2000

(30) Foreign Application Priority Data

Sep. 16, 1999 (CH) .............................................. 1700/99

(51) Int. Cl.⁷ .............................................. A01N 43/36
(52) U.S. Cl. ...................................................... 504/138
(58) Field of Search ........................................ 504/138

(56) References Cited

U.S. PATENT DOCUMENTS

| 5,441,992 A | | 8/1995 | Ort et al. | |
|---|---|---|---|---|
| 5,516,750 A | * | 5/1996 | Willms et al. | 504/106 |
| 5,627,131 A | | 5/1997 | Shribbs et al. | |
| 5,905,057 A | * | 5/1999 | Forget et al. | 504/116 |

FOREIGN PATENT DOCUMENTS

| DE | A-4331448 | | 3/1995 |
|---|---|---|---|
| EP | 496631 | * | 1/1992 |
| EP | A-0551650 | | 7/1993 |
| WO | WO-00/30447 | | 6/2000 |

OTHER PUBLICATIONS

Menendez et al, Meded.—Fac. Landbouwkd. Toegepaste Biol. Wet. (Univ. Gent), 63(3a), 761–7, 1998.*
"Enhancing the Margin of Selectivity of RPA 201772 in Zea Mays with Antidotes", Weed Science vol. 47, No. 5, 1999, pp. 492–497, XP000901419, ISSN: 0043–1745 p. 492, the abstract.

* cited by examiner

Primary Examiner—Alton Pryor
(74) Attorney, Agent, or Firm—William A. Teoli, Jr.; Thomas Hamilton

(57) ABSTRACT

A selective herbicidal composition for controlling grasses and weeds in crops of cultivated plants, comprising
  a) a herbicidally effective amount of a compound of formula I

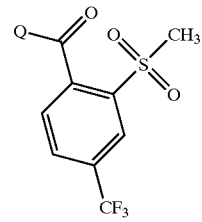
(I)

wherein
Q is the group

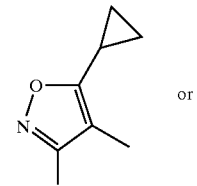
(Q₁)

or

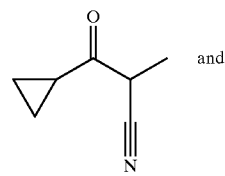
(Q₂)

and $R_1$ is hydrogen, $—COO—C_1-C_4$-alkyl, $—S—C_1-C_4$-alkyl or $—SO—C_1-C_4$-alkyl; and
b) to antagonise the herbicide, an antidotally effective amount of a safener of formula II

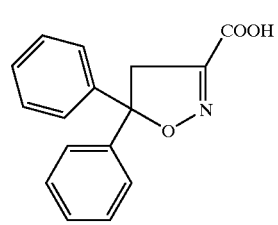
(II)

or the ethyl esters thereof.

12 Claims, No Drawings

HERBICIDAL COMPOSITION

The present invention relates to novel selective herbicidal compositions for controlling grasses and weeds in crops of cultivated plants, especially in crops of cereals and maize, which compositions comprise a herbicide and a safener (antidote) and protect the cultivated plants, but not the weeds, from the phytotoxic action of the herbicide, and to the use of said composition for controlling weeds in crops of cultivated plants.

When applying herbicides, the cultivated plants may also suffer severe damage owing to factors that include the concentration of the herbicide and the mode of application, the cultivated plant itself, the nature of the soil, and the climatic conditions such as exposure to light, temperature and rainfall. To counteract this problem and similar ones, the proposal has already been made to use different compounds as safeners which are able to antagonise the harmful action of the herbicide on the cultivated plant, i.e. to protect the cultivated plant while leaving the herbicidal action on the weeds to be controlled virtually unimpaired. It has, however, been found that the proposed safeners often have a very specific action with respect not only to the cultivated plants but also to the herbicide, and in some cases also subject to the mode of application, i.e. a specific safener will often be suitable only for a specific cultivated plant and a specific class of herbicide or a specific herbicide. Thus, for example, EP-A-0 551 650 discloses compounds that protect cultivated plants from the phytotoxic action of herbicides including 2-acylated 1,3-dicarbonyl compounds.

It has now been found that compounds of formula II

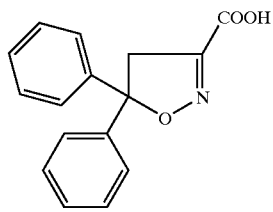
(II)

or the ethyl esters thereof are suitable for protecting cultivated plants from the phytotoxic action of a certain class of pyrazolyl herbicides.

Accordingly, the invention provides a selective herbicidal composition comprising, in addition to customary inert formulation assistants such as carriers, solvents and wetting agents, a mixture of a) a herbicidally effective amount of a herbicide of formula I

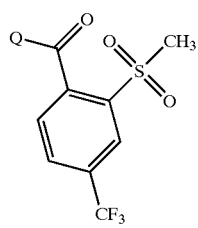
(I)

wherein
Q is the group

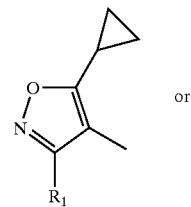
(Q₁)

or

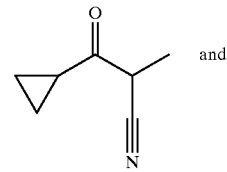
(Q₂)

and $R_1$ is hydrogen, $-COO-C_1-C_4$-alkyl, $-S-C_1-C_4$-alkyl or $-SO-C_1-C_4$-alkyl; and b) to antagonise the herbicide, an antidotally effective amount of a safener of formula II

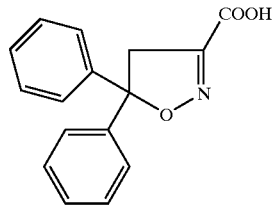
(II)

or the ethyl esters thereof.

The invention also relates to a method of selectively controlling weeds in crops of cultivated plants, which comprises treating said cultivated plants, the seeds or seedlings or the crop area thereof, concurrently or separately, with a herbicidally effective amount of the herbicide of formula I and, to antagonise the herbicide, an antidotally effective amount of the safener of formula II.

Suitable cultivated plants which can be protected by the safeners of formula II against the harmful action of the aforementioned herbicides are preferably cereals, cotton, soybean, sugar beet, sugar cane, plantations, rape, maize and rice, most particularly in maize.

Crops will also be understood as meaning those crops that have been made tolerant to herbicides or classes of herbicides by conventional breeding or genetic engineering methods.

The weeds to be controlled may be monocot as well as dicot weeds, typically Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola and Veronica.

Crop areas will be understood as meaning the areas already under cultivation with the cultivated plants or seeds thereof, as well as the areas intended for cropping with said cultivated plants.

Depending on the end use, a safener of formula II can be used for pretreating seeds of the crop plants (dressing of seeds or seedlings) or it can be incorporated in the soil before or after sowing. It can, however, also be applied by itself alone or together with the herbicide postemergence.

Treatment of the plant or the seeds with the safener can therefore in principle be carried out irrespective of the time of application of the herbicide. Treatment can, however, also be carried out by simultaneous application of the herbicide and safener (e.g. as tank mixture). The concentration of safener with respect to the herbicide will depend substantially on the mode of application. Where a field treatment is carried out either by using a tank mixture with a combination of safener and herbicide or by separate application of safener and herbicide, the ratio of safener to herbicide will usually be from 100:1 to 1:100, preferably 20:1 to 1:20.

In the context of the present invention, alkyl is methyl, ethyl, n-propyl, isopropyl, n-butyl, sec.-butyl, isobutyl and tert.-butyl.

The compound of formula I, wherein Q is $Q_1$ and $R_1$ is hydrogen, is known for example from the Pesticide Manual, eleventh ed., British Crop Protection Council, 1997. The remaining compounds of formula I are described e.g. in WO 97/43270 and in WO 99/51583. The compound of formula I, in which Q is $Q_2$, is described in EP-A-0 496 631. The compound of formula II is known from DE-A-4331448.

Preferred compositions according to the invention contain a compound of formula I, in which Q is $Q_1$ and $R_1$ is hydrogen, —$SOCH_3$ or —$SCH_3$.

In field treatment it is usual to apply 0.001 to 5.0 kg/ha, preferably 0.001 to 0.5 kg/ha, of safener.

The concentration of herbicide is usually in the range from 0.001 to 2 kg/ha, but will preferably be from 0.005 to 1 kg/ha.

The compositions of this invention are suitable for all methods of application commonly used in agriculture, including pre-emergence application, post-emergence application and seed dressing. For seed dressing, 0.001 to 10 g of safener/kg of seeds, preferably 0.05 to 2 g of safener/kg of seeds, is usually applied. If the safener is used in liquid form shortly before sowing to effect soaking, then it is preferred to use safener solutions that contain the active ingredient in a concentration of 1 to 10000 ppm, preferably of 100 to 1000 ppm. For application, it is preferred to process the safeners of formula II, or mixtures of the safeners of formula II and the herbicides of formula I, conveniently together with the customary formulation assistants to formulations, typically to emulsifiable concentrates, coatable pastes, directly sprayable or dilutable solutions, dilute emulsions, wettable powders, soluble powders, dusts, granulates or microcapsules. Such formulations are described, for example, in WO 97/34485, pages 9 to 13. The formulations are prepared in known manner, conveniently by homogeneously mixing and/or grinding the active ingredients with liquid or solid formulation assistants, typically solvents or solid carriers. Surface-active compounds (surfactants) may additionally be used for preparing the formulations. Suitable solvents and solid carriers for this purpose are also described in said WO 97/34485, page 6.

Depending on the type of herbicide of formula I to be formulated, suitable surface-active compounds are nonionic, cationic and/or anionic surfactants and surfactant mixtures having good emulsifying, dispersing and wetting properties. Examples of suitable anionic, nonionic, and cationic surfactants are listed for example in said WO 97/34485, pages 7 to 8. Also the surfactants customarily for the art of formulation and described, inter alia, in "Mc Cutcheon's Detergents and Emulsifiers Annual" MC Publishing Corp., Ridgewood N.J., 1981, Stache, H., "Tensid-Taschenbuch" (Handbook of Surfactants), Carl Hanser Verlag, Munich/Vienna, 1981, and M. and J. Ash, "Encyclopedia of Surfactants", Vol I–III, Chemical Publishing Co., New York, 1980–81 are suitable for manufacture of the herbicidal compositions according to the invention.

The herbicidal compositions will usually contain from 0.1 to 99% by weight, preferably from 0.1 to 95% by weight, of compound mixture of the compound of formula I and the compounds of formulae II, from 1 to 99.9% by weight of a solid or liquid formulation assistant, and from 0 to 25% by weight, preferably from 0.1 to 25% by weight, of a surfactant. Whereas it is customarily preferred to formulate commercial products as concentrates, the end user will normally use dilute formulations.

The compositions may also contain further ingredients, such as stabilisers, e.g. where appropriate epoxidised vegetable oils (epoxidised coconut oil, rapeseed oil, or soybean oil), antifoams, typically silicone oil; preservatives, viscosity regulators, binders, and tackifiers, as well as fertilisers or other chemical agents. Different methods and techniques may suitably be used for applying the safeners of formula II or compositions containing them for protecting cultivated plants from the harmful effects of herbicides of formula I, conveniently the following:

i) Seed Dressing a) Dressing the seeds with a wettable powder formulation of the compound of formula II by shaking in a vessel until the safener is uniformly distributed on the surface of the seeds (dry treatment), using about 1 to 500 g of compound of formula II (4 g to 2 kg of wettable powder) per 100 kg of seeds.

b) Dressing seeds with an emulsifiable concentrate of the compound of formula II by method a) (wet treatment).

c) Dressing by immersing the seeds in a mixture containing 100–1000 ppm of compound of formula II for 1 to 72 hours and where appropriate subsequently drying them (seed soaking).

Seed dressing or treatment of the germinated seedlings is naturally the preferred method of application, because the safener treatment is fully concentrated on the target crop. Usually 1 to 1000 g, preferably 5 to 250 g, of safener is used per 100 kg of seeds. However, depending on the method employed, which also permits the use of other chemical agents or micronutrients, the concentrations may deviate above or below the indicated limit values (repeat dressing).

ii) Application as a Tank Mixture

A liquid formulation of a mixture of safener and herbicide (reciprocal ratio from 10:1 to 1:100) is used, the concentration of herbicide being from 0.005 to 5.0 kg/ha. This tank mixture is applied before or after sowing.

iii) Application in the Furrow

The compound of formula II formulated as emulsifiable concentrate, wettable powder or granulate is applied to the open furrow in which the seeds have been sown. After covering the furrow, the herbicide is applied pre-emergence in conventional manner.

iv) Controlled Release of Compound

The compound of formula II is applied in solution to a mineral granular carrier or to polymerised granules (urea/formaldehyde) and then dried. A coating can then be applied (coated granules) that allows the safenerto be released at a controlled rate over a specific period of time.

Particularly preferred formulations are made up as follows (%=per cent by weight; compound mixture means the mixture of the compound of formula I with the compound of formula II):

Emulsifiable Concentrates

Compound mixture: 1 to 90%, preferrably 5 to 20%

Surfactant: 1 to 30%, preferably 10 to 20%

Liquid carrier: 5 to 94%, preferably 70 to 85%

Dusts

Compound mixture: 0.1 to 10%, preferably 0,1 to 5%
Solid carrier: 99.9 to 90%, preferably 99.9 to 99%

Suspension Concentrates

Compound mixture: 5 to 75%, preferably 10 to 50%
Water: 94 to 24%, preferably 88 to 30%
Surfactant: 1 to 40%, preferably 2 to 30%

Wettable Powders

Compound mixture: 0.5 to 90%, preferably 1 to 80%
Surfactant: 0.5 to 20%, preferably 1 to 15%
Solid carrier: 5 to 95%, preferably 15 to 90%

Granulates

Compound mixture: 0.1 to 30%, preferably 0.1 to 15%
Solid carrier: 99.5 to 70%, preferably 97 to 85%

The invention is illustrated in more detail by the following non-limitative Examples.

Formulation Examples for Mixtures of Herbicides of Formula I and Safeners of Formula II (%=Percent by Weight)

| F1. Emulsifiable concentrates | a) | b) | c) | d) |
|---|---|---|---|---|
| Compound mixture | 5% | 10% | 25% | 50% |
| Calcium dodecylbenzenesulfonate | 6% | 8% | 6% | 8% |
| Polyethoxylated castor oil (36 mol EO) | 4% | — | 4% | 4% |
| Octylphenol polyethoxylate (7–8 mol EO) | — | 4% | — | 2% |
| Cyclohexanone | — | — | 10% | 20% |
| Aromatic hydrocarbon mixture $C_9$–$C_{12}$ | 85% | 78% | 55% | 16% |

Emulsions of any desired concentration can be prepared by diluting such concentrates with water.

| F2. Solutions | a) | b) | c) | d) |
|---|---|---|---|---|
| Compound mixture | 5% | 10% | 50% | 90% |
| 1-Methoxy-3-(3-methoxy-propoxy)propane | — | 20% | 20% | — |
| Polyethylene glycol MG 400 | 20% | 10% | — | — |
| N-Methyl-2-pyrrolidone | — | — | 30% | 10% |
| Aromatic hydrocarbon mixture $C_9$–$C_{12}$ | 75% | 60% | — | — |

The solutions are suitable for use as microdrops.

| F3. Wettable powders | a) | b) | c) | d) |
|---|---|---|---|---|
| Compound mixture | 5% | 25% | 50% | 80% |
| Sodium ligninsulfonate | 4% | — | 3% | — |
| Sodium lauryl sulfate | 2% | 3% | — | 4% |
| Sodium diisobutylnaphthalenesulfonate | — | 6% | 5% | 6% |
| Octylphenol polyethoxylate (7–8 mol EO) | — | 1% | 2% | — |
| Highly dispersed silica | 1% | 3% | 5% | 10% |
| Kaolin | 88% | 62% | 35% | — |

The compound is thoroughly mixed with the adjuvants and this mixture is ground in a suitable mill to give wettable powders which can be diluted with water to give suspensions of any desired concentration.

| F4. Coated granulates | a) | b) | c) |
|---|---|---|---|
| Compound mixture | 0.1% | 5% | 15% |
| Highly dispersed silica | 0.9% | 2% | 2% |
| Inorganic carrier | 99.0% | 93% | 83% |

| F4. Coated granulates | a) | b) | c) |
|---|---|---|---|
| (Æ 0.1–1 mm) such as $CaCO_3$ or $SiO_2$ | | | |

The compound is dissolved in dichloromethane, the solution is sprayed on to the carrier, and the solvent is removed under vacuum.

| F5. Coated granulates | a) | b) | c) |
|---|---|---|---|
| Compound mixture | 0.1% | 5% | 15% |
| Polyethylene glycol MG 200 | 1.0% | 2% | 3% |
| Highly dispersed silica | 0.9% | 1% | 2% |
| Inorganic carrier (Æ 0.1–1 mm) such as $CaCO_3$ or $SiO_2$ | 98.0% | 92% | 80% |

The finely ground compound is uniformly applied in a mixer to the carrier moistened with polyethylene glycol. Non-dusty coated granulates are obtained in this manner.

| F6. Extruder granulates | a) | b) | c) | d) |
|---|---|---|---|---|
| Compound mixture | 0.1% | 3% | 5% | 15% |
| Sodium ligninsulfonate | 1.5% | 2% | 3% | 4% |
| Carboxymethylcellulose | 1.4% | 2% | 2% | 2% |
| Kaolin | 97.0% | 93% | 90% | 79% |

The compound is mixed and ground with the adjuvants, and the mixture is moistened with water. This mixture is extruded and then dried in a stream of air.

| F7. Dusts | a) | b) | c) |
|---|---|---|---|
| Compound mixture | 0.1% | 1% | 5% |
| Talc | 39.9% | 49% | 35% |
| Kaolin | 60.0% | 50% | 60% |

Ready-for-use dusts are obtained by mixing the active ingredient with the carriers on a suitable mill.

| F8. Suspension concentrates | a) | b) | c) | d) |
|---|---|---|---|---|
| Compound mixture | 3% | 10% | 25% | 50% |
| Ethylene glycol | 5% | 5% | 5% | 5% |
| Nonylphenol polyethoxylate (15 mol EO) | — | 1% | 2% | — |
| Sodium ligninsulfonate | 3% | 3% | 4% | 5% |
| Carboxymethylcellulose | 1% | 1% | 1% | 1% |
| 37% aqueous formaldehydesolution | 0.2% | 0.2% | 0.2% | 0.2% |
| Silicone oil emulsion | 0.8% | 0.8% | 0.8% | 0.8% |
| Water | 87% | 79% | 62% | 38% |

The finely ground compound is intimately mixed with the adjuvants to give a suspension concentrate from which suspensions of any desired concentration can be prepared by dilution with water.

It is often expedient to formulate the compound of formula I and the components of formula II individually and then to combine them shortly before application in the applicator in the desired mixture ratio as tank mixture in water.

The following Examples illustrate the ability of the safeners of formula II to protect cultivated plants from the phytotoxic action of herbicides of formula I.

BIOLOGICAL EXAMPLES

Example B1
Post-emergence Test

The test plants are raised in pots under greenhouse conditions until reaching a post-application stage. Standard soil is used as the growing medium. In a post-emergence stage, the herbicides are applied to the test plants both on their own and in a mixture with safeners, or are applied to crop plants raised from seed previously dressed with safeners. The rates of application depend on the optimum dosages determined under field or greenhouse conditions. Evaluation of the tests is made after 2 to 4 weeks (% action=completely dead; 0% action=no phytotoxic action). The mixtures used in this test show good results.

Examples of the safening action of the compounds of formula II are given in Table B1. The application rate of compound of formula I is 50 g/ha, and the application rate of compound of formula II is likewise 50 g/ha:

TABLE B3

Safening action of the compounds of formula II for the compound of formula I, in which Q is $Q_1$ and $R_1$ is hydrogen (formula Ia):

| plant | compound of formula Ia: | compound of formula Ia + compound of formula II as the ethyl ester | compound of formula Ia + compound of formula II |
|---|---|---|---|
| | phytotoxic action | | |
| maize | 20 | 15 | 10 |
| Chenopodium | 100 | 100 | 100 |

The above data show that, by using the mixture according to the invention, the phytotoxic action of the compound of formula Ia on maize at an application rate of 50 g/ha can be reduced from an agronomically intolerable 20% to 15% or only 10% without impairing the good herbicidal action on Chenopodium.

The same results are obtained by formulating the compound mixture in accordance with the other above-mentioned formulation examples.

What is claimed is:
1. A selective herbicidal composition comprising, in addition to customary inert formulation assistants, a mixture of
   a) a herbicidally effective amount of a compound of formula I

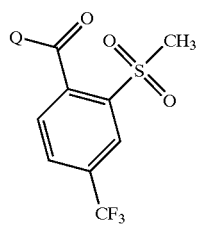

(I)

wherein
Q is the group

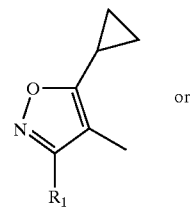 or ($Q_1$)

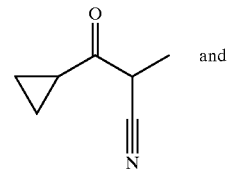 and ($Q_2$)

$R_1$ is hydrogen, —COO—$C_1$–$C_4$-alkyl, —S—$C_1$–$C_4$alkyl or —SO—$C_1$–$C_4$alkyl; and b) to antagonise the herbicide, an antidotally effective amount of a safener of formula II

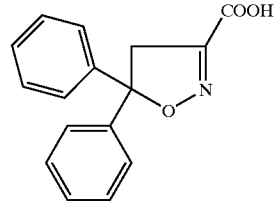

(II)

2. A method of selectively controlling weeds and grasses in crops of cultivated plants, which comprises treating said cultivated plants, the seeds or seedlings or the crop area thereof, concurrently or separately, with a herbicidally effective amount of the compound of formula I according to claim 1 and, to antagonise the herbicide, an antidotally effective amount of the safener of formula II according to claim 1.

3. The method according to claim 2, wherein the cultivated plants are maize.

4. A selective herbicidal composition comprising, in addition to customary inert formulation assistants, a mixture of
   a) a herbicidally effective amount of a compound of formula I

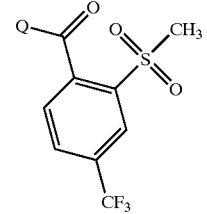

(I)

wherein
Q is the group

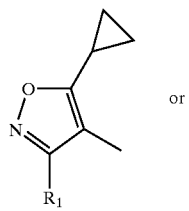 (Q₁)

or

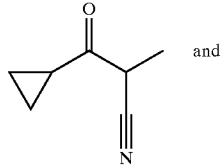 (Q₂)

and $R_1$ is —COO—$C_1$-$C_4$-alkyl, —S—$C_1$-$C_4$-alkyl or —SO—$C_1$-$C_4$-alkyl; and b) to antagonise the herbicide, an antidotally effective amount of a safener of formula II

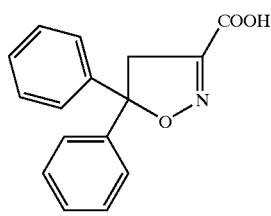 (II)

5. A method of selectively controlling weeds and grasses in crops of cultivated plants, which comprises treating said cultivated plants, the seeds or seedlings or the crop area thereof, concurrently or separately, with a herbicidally effective amount of the compound of formula I according to claim 4 and, to antagonise the herbicide, an antidotally effective amount of the safener of formula II according to claim 4.

6. The method according to claim 5, wherein the cultivated plants are maize.

7. A selective herbicidal composition comprising, in addition to customary inert formulation assistants, a mixture of a) a herbicidally effective amount of a compound of formula I

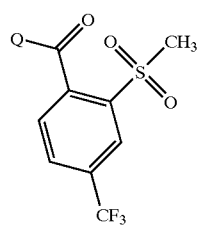 (I)

wherein
Q is the group

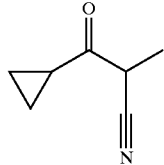 (Q₂)

and b) to antagonise the herbicide, an antidotally effective amount of a safener of formula II

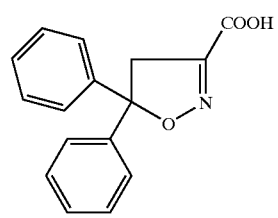 (II)

8. A method of selectively controlling weeds and grasses in crops of cultivated plants, which comprises treating said cultivated plants, the seeds or seedlings or the crop area thereof, concurrently or separately, with a herbicidally effective amount of the compound of formula I according to claim 7 and, to antagonise the herbicide, an antidotally effective amount of the safener of formula II according to claim 7.

9. The method according to claim 8, wherein the cultivated plants are maize.

10. A selective herbicidal composition comprising, in addition to customary inert formulation assistants, a mixture of a) a herbicidally effective amount of a compound of formula I

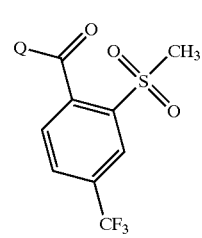 (I)

wherein
Q is the group

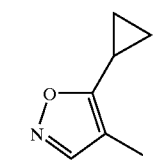 (Q₁)

and b) to antagonise the herbicide, an antidotally effective amount of a safener of formula II

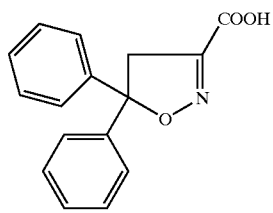
(II)

11. A method of selectively controlling weeds and grasses in crops of cultivated plants, which comprises treating said cultivated plants, the seeds or seedlings or the crop area thereof, concurrently or separately, with a herbicidally effective amount of the compound of formula I according to claim 10 and, to antagonise the herbicide, an antidotally effective amount of the safener of formula II according to claim 10.

12. The method according to claim 11, wherein the cultivate plants are maize.

* * * * *